(12) United States Patent
Fox

(10) Patent No.: US 9,913,724 B2
(45) Date of Patent: Mar. 13, 2018

(54) MENISCUS PROSTHETIC DEVICE

(71) Applicant: Active Implants Corporation, Memphis, TN (US)

(72) Inventor: Howard Fox, Roslyn, NY (US)

(73) Assignee: Active Implants LLC, Memphis, TN (US)

( * ) Notice: Subject to any disclaimer, the term of this patent is extended or adjusted under 35 U.S.C. 154(b) by 0 days.

(21) Appl. No.: 15/601,913

(22) Filed: May 22, 2017

(65) Prior Publication Data

US 2017/0252174 A1    Sep. 7, 2017

Related U.S. Application Data

(60) Division of application No. 15/134,192, filed on Apr. 20, 2016, now Pat. No. 9,655,730, which is a continuation of application No. 13/481,338, filed on May 25, 2012, now Pat. No. 9,320,606, which is a continuation of application No. 11/868,254, filed on Oct. 5, 2007, now Pat. No. 8,192,491.

(60) Provisional application No. 60/828,770, filed on Oct. 9, 2006.

(51) Int. Cl.
　　*A61F 2/38*　　　(2006.01)
　　*A61L 27/18*　　　(2006.01)
　　*A61F 2/30*　　　(2006.01)

(52) U.S. Cl.
　　CPC ............ *A61F 2/3872* (2013.01); *A61L 27/18* (2013.01); *A61F 2/30942* (2013.01); *A61F 2/30965* (2013.01); *A61F 2002/30069* (2013.01); *A61F 2002/30673* (2013.01); *A61F 2002/30884* (2013.01); *A61F 2002/3895* (2013.01)

(58) Field of Classification Search
　　CPC ........................... A61F 2/3872; A61F 2/30965
　　See application file for complete search history.

(56) References Cited

U.S. PATENT DOCUMENTS

| 3,551,560 A | 12/1970 | Thiele |
| 3,703,575 A | 11/1972 | Thiele |
| 4,085,466 A | 4/1978 | Goodfellow et al. |
| 4,344,193 A | 8/1982 | Kenny |

(Continued)

FOREIGN PATENT DOCUMENTS

| EP | 1426023 | 6/2004 |
| WO | WO 03/061522 | 7/2003 |

(Continued)

OTHER PUBLICATIONS

United States, International Searching Authority, Notification of Transmittal of the International Search Report and the Written Opinion of the International Searching Authority, or the Declaration, International Application No. PCT/US2007/080625, International Search report dated Apr. 16, 2008, 3 pages.

(Continued)

*Primary Examiner* — Bruce E Snow
*Assistant Examiner* — Melissa Hoban
(74) *Attorney, Agent, or Firm* — Haynes and Boone, LLP

(57) ABSTRACT

A prosthetic device that may be utilized as an artificial meniscus is disclosed. The prosthetic device can restore shock absorption, stability, and function to the knee after the damaged natural meniscus is removed and replaced with the prosthetic device. In some embodiments, the meniscus includes an integral fixation anchor and additional features that minimize the requirement for modification of the implant for proper fit during surgery.

12 Claims, 8 Drawing Sheets

(56) References Cited

U.S. PATENT DOCUMENTS

| | | |
|---|---|---|
| 4,385,404 A | 5/1983 | Sully et al. |
| 4,502,161 A | 3/1985 | Wall |
| 4,693,722 A | 9/1987 | Wall |
| 4,728,332 A | 3/1988 | Albrektsson |
| 4,880,429 A | 11/1989 | Stone |
| 4,919,667 A | 4/1990 | Richmond |
| 4,936,862 A | 6/1990 | Walker et al. |
| 5,007,934 A | 4/1991 | Stone |
| 5,092,894 A | 3/1992 | Kenny |
| 5,116,374 A | 5/1992 | Stone |
| 5,158,574 A | 10/1992 | Stone |
| 5,171,322 A | 12/1992 | Kenny |
| 5,306,311 A | 4/1994 | Stone et al. |
| 5,344,459 A | 9/1994 | Swartz |
| 5,352,463 A | 10/1994 | Badylak et al. |
| 5,358,525 A | 10/1994 | Fox et al. |
| 5,358,531 A | 10/1994 | Goodfellow |
| 5,624,463 A | 4/1997 | Stone et al. |
| 5,681,353 A | 10/1997 | Li et al. |
| 5,735,903 A | 4/1998 | Li et al. |
| 5,769,899 A | 6/1998 | Schwartz et al. |
| 5,782,915 A | 7/1998 | Stone |
| 5,865,849 A | 2/1999 | Stone |
| 5,871,842 A | 2/1999 | Goodfellow |
| 5,913,900 A | 6/1999 | Stone |
| 5,922,027 A | 7/1999 | Stone |
| 5,944,755 A | 8/1999 | Stone |
| 5,944,759 A | 8/1999 | Link |
| 5,984,858 A | 11/1999 | Stone |
| 6,042,610 A | 3/2000 | Li et al. |
| 6,046,379 A | 4/2000 | Stone et al. |
| 6,049,025 A | 4/2000 | Stone et al. |
| 6,056,777 A | 5/2000 | McDowell |
| 6,093,204 A | 7/2000 | Stone |
| 6,126,690 A | 10/2000 | Ateshian et al. |
| 6,148,818 A | 11/2000 | Pagan |
| 6,161,080 A | 12/2000 | Aouni-Ateshian et al. |
| 6,176,880 B1 | 1/2001 | Plouhar et al. |
| 6,205,411 B1 | 3/2001 | DiGioia et al. |
| 6,206,927 B1 | 3/2001 | Fell et al. |
| 6,231,608 B1 | 5/2001 | Stone |
| 6,251,143 B1 | 6/2001 | Schwartz et al. |
| 6,267,786 B1 | 7/2001 | Stone |
| 6,306,169 B1 | 10/2001 | Lee et al. |
| 6,371,958 B1 | 4/2002 | Overaker |
| 6,455,309 B2 | 9/2002 | Stone |
| 6,468,314 B2 | 10/2002 | Schwartz et al. |
| 6,511,511 B1 | 1/2003 | Slivka et al. |
| 6,530,956 B1 | 3/2003 | Mansmann |
| 6,558,421 B1 | 5/2003 | Fell et al. |
| 6,575,986 B2 | 6/2003 | Overaker |
| 6,626,950 B2 | 9/2003 | Brown et al. |
| 6,629,997 B2 | 10/2003 | Mansmann |
| 6,652,587 B2 | 11/2003 | Felt et al. |
| 6,679,914 B1 | 1/2004 | Gabbay |
| 6,699,252 B2 | 3/2004 | Farr, II et al. |
| 6,743,232 B2 | 6/2004 | Overaker et al. |
| 6,758,865 B1 | 7/2004 | Stone et al. |
| 6,783,712 B2 | 8/2004 | Slivka et al. |
| 6,852,330 B2 | 2/2005 | Bowman et al. |
| 6,884,428 B2 | 4/2005 | Binette et al. |
| 6,916,341 B2 | 7/2005 | Rolston |
| 6,966,928 B2 | 11/2005 | Fell et al. |
| 6,976,999 B2 | 12/2005 | Charlebois et al. |
| 6,989,034 B2 | 1/2006 | Hammer et al. |
| 6,994,730 B2 | 2/2006 | Posner |
| 7,124,762 B2 | 10/2006 | Carter et al. |
| 7,163,563 B2 | 1/2007 | Schwartz et al. |
| 7,201,917 B2 | 4/2007 | Malaviya et al. |
| 7,239,937 B2 | 7/2007 | Slemker et al. |
| 7,282,165 B2 | 10/2007 | Williams et al. |
| 7,291,169 B2 | 11/2007 | Hodorek |
| 7,297,161 B2 | 11/2007 | Fell |
| 7,341,602 B2 | 3/2008 | Fell et al. |
| 7,353,153 B2 | 4/2008 | Ascenzi et al. |
| 7,366,124 B2 | 5/2008 | Chun et al. |
| 7,383,164 B2 | 6/2008 | Aram et al. |
| 7,388,972 B2 | 6/2008 | Kitson |
| 7,572,295 B2 | 8/2009 | Steinberg |
| 7,594,934 B2 | 9/2009 | Stone |
| 7,611,653 B1 | 11/2009 | Elsner et al. |
| 7,796,791 B2 | 9/2010 | Tsougarakis et al. |
| 7,919,112 B2 | 4/2011 | Pathak et al. |
| 7,943,678 B2 | 5/2011 | Heijkants et al. |
| 7,991,599 B2 | 6/2011 | Linder-Ganz et al. |
| 8,016,884 B2 | 9/2011 | Shterling et al. |
| 8,108,190 B2 | 1/2012 | Riener et al. |
| 8,119,152 B2 | 2/2012 | Shikinami |
| 8,192,491 B2 | 6/2012 | Fox |
| 8,197,837 B2 | 6/2012 | Jamiolkowski et al. |
| 8,361,147 B2 | 1/2013 | Shterling et al. |
| 8,657,881 B2 | 2/2014 | Kladakis et al. |
| 2001/0016772 A1 | 8/2001 | Lee et al. |
| 2002/0022884 A1 | 2/2002 | Mansmann |
| 2002/0127265 A1 | 9/2002 | Bowman et al. |
| 2003/0013975 A1 | 1/2003 | Kiani |
| 2003/0060884 A1 | 3/2003 | Fell et al. |
| 2004/0006393 A1 | 1/2004 | Burkinshaw |
| 2004/0006394 A1 | 1/2004 | Lipman |
| 2004/0034418 A1 | 2/2004 | Li et al. |
| 2004/0098127 A1 | 5/2004 | Charlebois et al. |
| 2004/0117014 A1 | 6/2004 | Bryant |
| 2004/0147927 A1 | 7/2004 | Tsougarakis et al. |
| 2004/0153079 A1 | 8/2004 | Tsougarakis et al. |
| 2004/0167630 A1 | 8/2004 | Rolston |
| 2004/0175408 A1 | 9/2004 | Chun et al. |
| 2004/0195727 A1 | 10/2004 | Stoy |
| 2004/0199249 A1 | 10/2004 | Fell |
| 2004/0243250 A1 | 12/2004 | Stone et al. |
| 2005/0038520 A1 | 2/2005 | Binette et al. |
| 2005/0085915 A1 | 4/2005 | Steinberg |
| 2005/0113938 A1 | 5/2005 | Jamiolkowski et al. |
| 2005/0171604 A1 | 8/2005 | Michalow |
| 2005/0177249 A1 | 8/2005 | Kladakis et al. |
| 2005/0221703 A1 | 10/2005 | Stone |
| 2005/0234549 A1 | 10/2005 | Kladakis et al. |
| 2005/0236742 A1 | 10/2005 | Williams et al. |
| 2005/0278025 A1 | 12/2005 | Ku et al. |
| 2006/0002967 A1 | 1/2006 | Smestad et al. |
| 2006/0111726 A1 | 5/2006 | Felt et al. |
| 2006/0190078 A1 | 8/2006 | Fell |
| 2006/0190086 A1 | 8/2006 | Clemow |
| 2007/0015894 A1 | 1/2007 | Heijkants et al. |
| 2007/0038070 A1 | 2/2007 | Tank |
| 2007/0067032 A1 | 3/2007 | Felt et al. |
| 2007/0100447 A1 | 5/2007 | Steinberg |
| 2007/0123991 A1 | 5/2007 | Steinberg |
| 2007/0233269 A1 | 10/2007 | Steines et al. |
| 2007/0254005 A1 | 11/2007 | Pathak et al. |
| 2007/0299532 A1 | 12/2007 | Rhodes |
| 2008/0086210 A1 | 4/2008 | Fox |
| 2008/0097605 A1 | 4/2008 | Pastorello et al. |
| 2008/0097606 A1 | 4/2008 | Cragg |
| 2008/0183291 A1 | 7/2008 | Scheller et al. |
| 2008/0243202 A1 | 10/2008 | Lee |
| 2008/0262615 A1 | 10/2008 | De Villiers et al. |
| 2008/0262629 A1 | 10/2008 | Fonte |
| 2009/0012615 A1 | 1/2009 | Fell |
| 2009/0036984 A1 | 2/2009 | Hagen et al. |
| 2009/0259311 A1 | 10/2009 | Shterling et al. |

FOREIGN PATENT DOCUMENTS

| | | |
|---|---|---|
| WO | WO 2006/097932 | 9/2005 |
| WO | WO 2006/036352 | 4/2006 |
| WO | WO 2006/118822 | 11/2006 |

OTHER PUBLICATIONS

Sommerlath et al., "The Effects of an Artificial Meniscus Substitute in a Knee Joint With Resected Anterior Cruciate Ligament," Clinical Orthopaedics and Related Research, No. 289, pp. 276-284, J.B. Lippincott Company, Apr. 1993, 9 pages.

(56) References Cited

OTHER PUBLICATIONS

Van Arkel et al., "Human Meniscal Transplantation," British Editorial Society of Bone and Joint Surgery, The Journal of Bone and Joint Surgery, vol. 77-B, No. 4, Jul. 1995, 7 pages.
Messner et al., "The menisci of the knee joint. Anatomical and functional characteristics, and a rationale for clinical treatment," J. Anal. (1998) 193, pp. 161-178, Sports Medicine, Faculty of Health Sciences, Linkoping University, Sweden, May 12, 1998, 18 pages.
Rodkey, et al., "A Clinical Study of Collagen Meniscus Implants to Restore the Injured Meniscus," Clinical Orthopaedics and Related Research, No. 367S, pp. S281-5292, 1999 Lippincott Williams & Wilkins, Inc., Oct. 1999, 12 pages.
Cole, et al., "Allograft Meniscal Transplantation: Background, Techniques, and Results," The Journal of Bone & Joint Surgery, vol. 84:1236-1250, No. 7, Jul. 2002, 17 pages.
Cole, et al., "Prospective Evaluation of Allograft Meniscus Transplantation: A Minimum 2-Year Follow-up," The American Journal of Sports Medicine, vol. 34, No. 6, Mar. 2003, 9 pages.
Hallock, et al., "Unicompartmental Tibial Hemiarthroplasty: Early Results of the UniSpacer Knee," Clinical Orthopaedics and Related Research, No. 416, pp. 154-163, Lippincott Williams & Wilkins, Inc., Nov. 2003, 10 pages.
Scott, "The UniSpacer: Insufficient Data to Support its Widespread Use," Clinical Orthopaedics and Related Research, No. 416, pp. 164-166, Lippincott Williams & Wilkins, Inc., Nov. 2003, 3 pages.
Kobayashi, et al., "A two year in vivo study of polyvinyl alcohol-hydrogel (PVA-H) artificial meniscus," Orthopedic Surgery Dept., Osaka Medical College, Osaka, Japan, Department of Tissue Regeneration, Institute for Frontier Medical Sciences, Kyoto University, Japan, Elsevier Biomaterials 26 (2005) pp. 3243-3248, www.elsevier.com/locate/biomaterials; 2004 Elsevier Ltd., 6 pages.
Sisto et al., "UniSpacer, Arthroplasty of the Knee," Los Angeles Orthopaedic Institute; Sherman Oaks, California, The Journal of Bone and Joint Surgery, Incorporated, 2005: 87:1706-1711, 7 pages.
Zaffagnini et al., "Arthroscopic collagen meniscus implant results at 6 to 8 years follow up," Knee Surg Sports Traumatol Arthrosc (2007) 151:75-183, Springer-Verlag, 2006, 9 pages.
Tien En et al., "Replacement of the Knee Meniscus by a Porous Polymer Implant: A Study in Dogs," The American Journal of Sports Medicine, vol. 34, No. 1, 2006, 8 pages.
Hommen et al., "Meniscus Allograft Transplantation: Ten-Year Results of Cryopreserved Allografts," Arthroscopy: The Journal of Arthroscopic and Related Surgery, vol. 23, No. 4 (Apr.), 2007, pp. 388-393, 9 pages.
Farr et al., "Concomitant Meniscal Allograft Transplantation and Autologous Chondrocyte Implantation: Minimum 2-Year Follow-up," The American Journal of Sports Medicine, vol. 35, No. 9, 2007, American Orthopaedic Society for Sports Medicine, 8 pages.
International Search Report and Written Opinion of the International Searching Authority, International Application No. PCT/US2008/059770, dated Sep. 3, 2008, 8 pages.
Fowler, Senta; et al., "Information Sharing of Prosthetic Parts CAD Databases," IEEE, 1995, pp. 82-87.
Chen, Jim X., et al., "Knee Surgery Assistance: patient Model construction, Motion Simulation, and Biomechanical Visualization," IEEE, 2001, PQS, 1042-1052.
International Searching Authority/European Patent Office, "International Search Report and Written Opinion" for PCT/US2009/039874, dated Jul. 9, 2010, 21 pages.
European Search Report received in European Patent Application No. 07853818.8, dated Jun. 19, 2012, 6 pages.
European Patent Office, "Examination Report" for Application No. 07853818.8, dated Nov. 20, 2014.

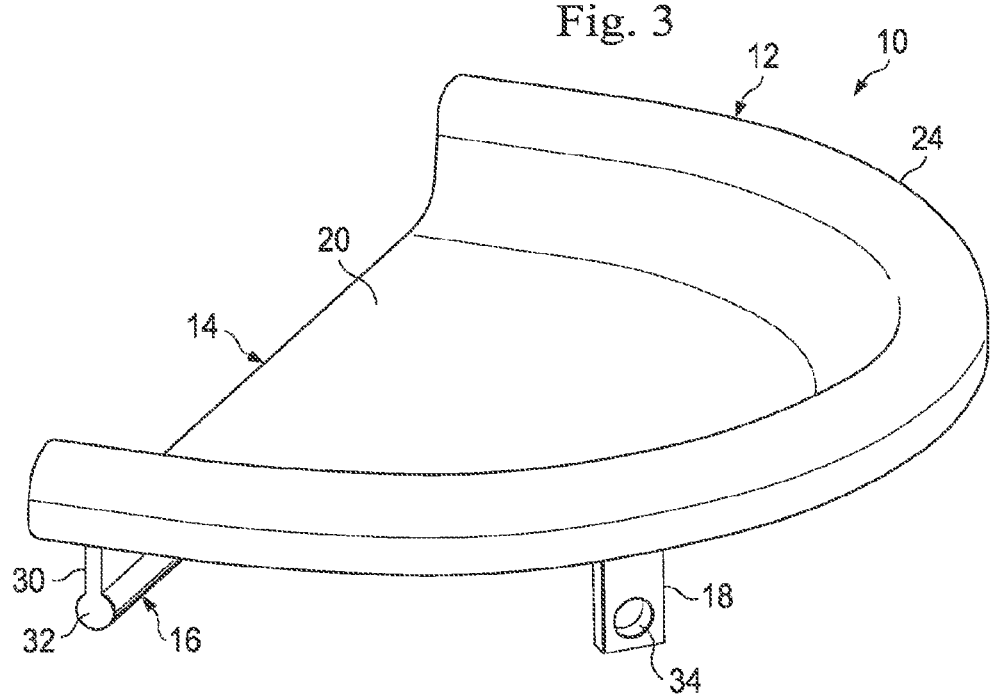
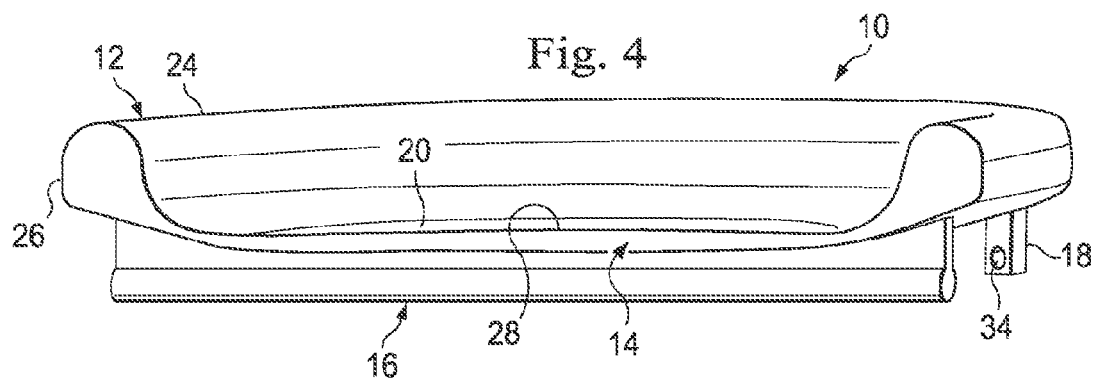

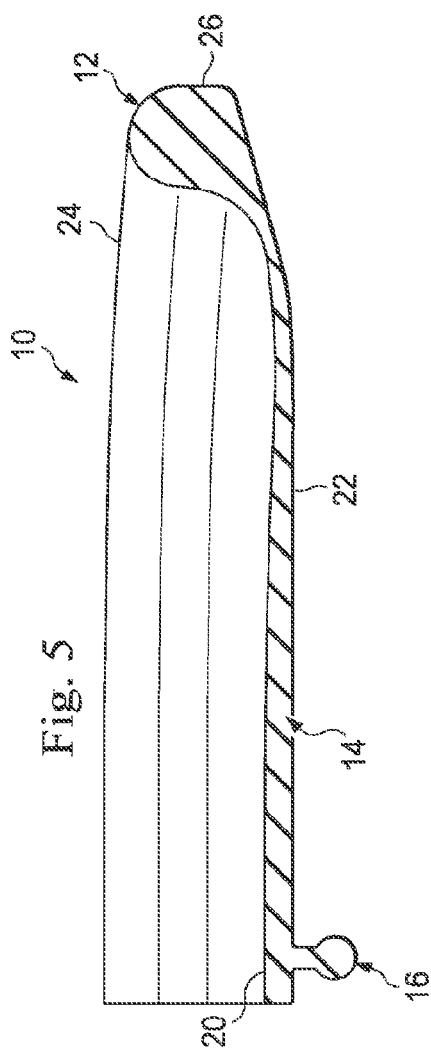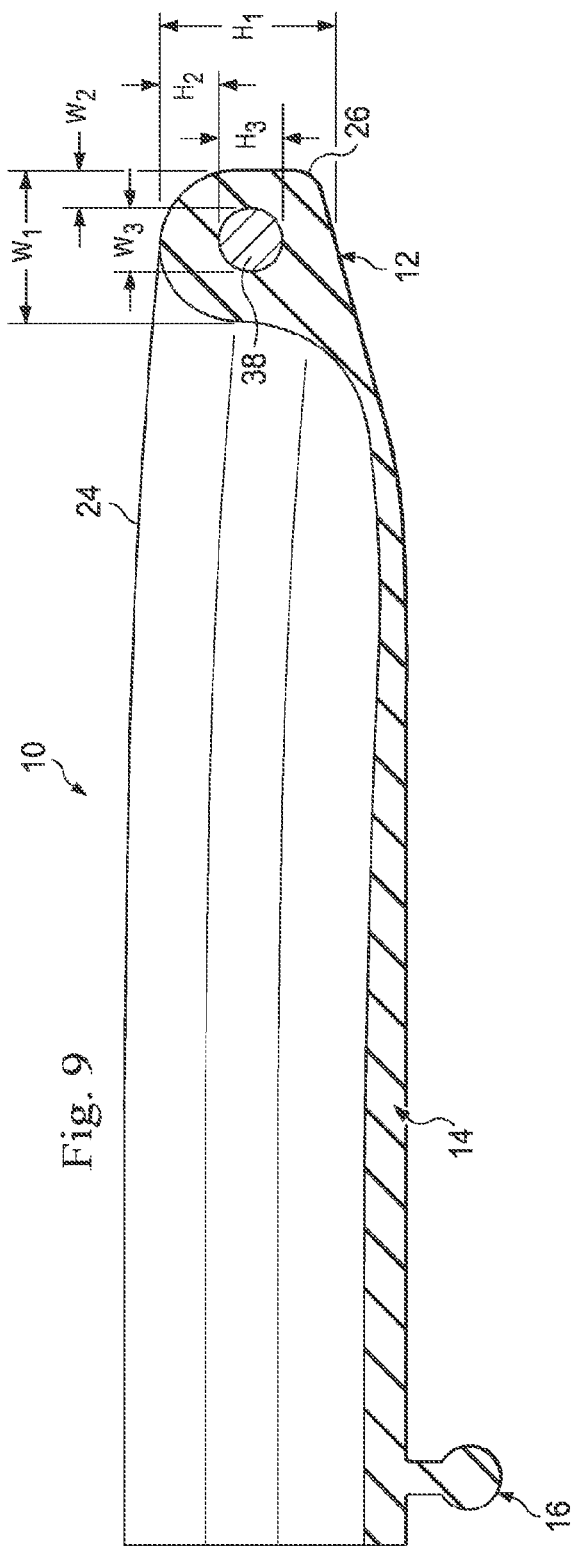

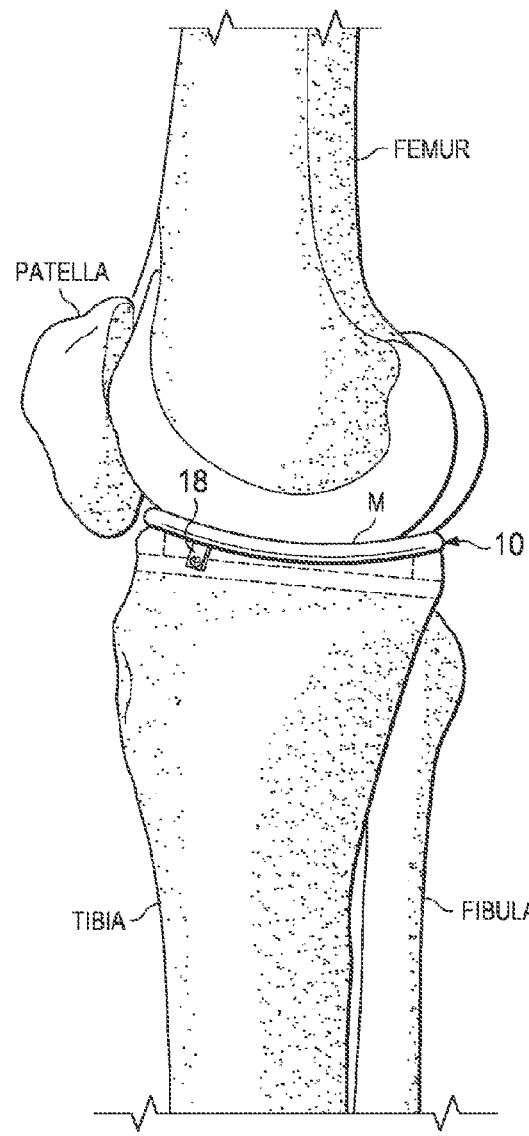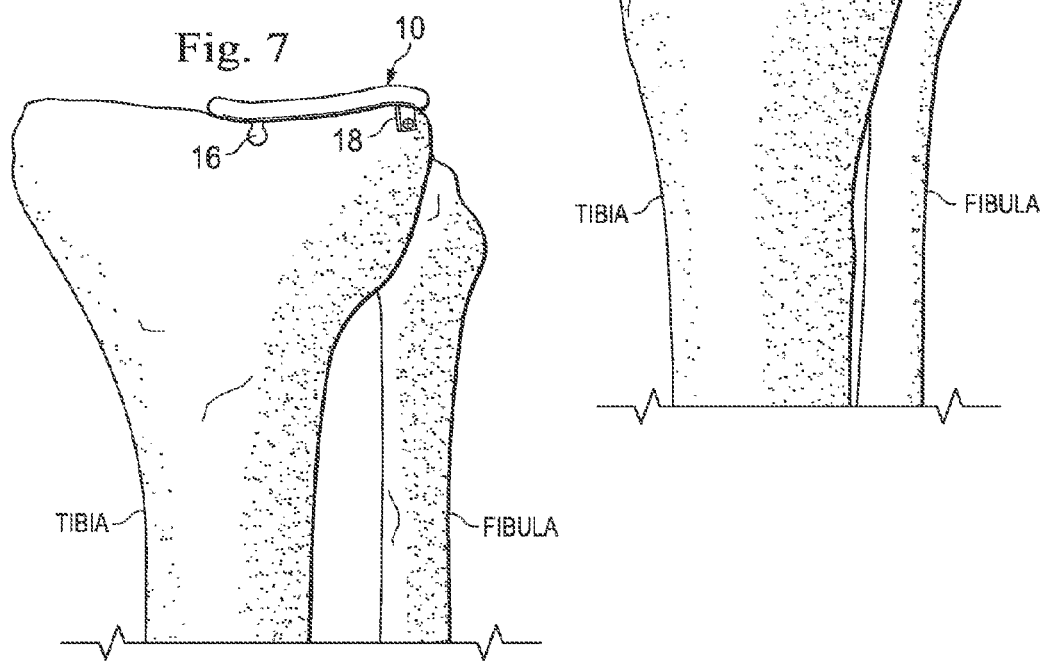

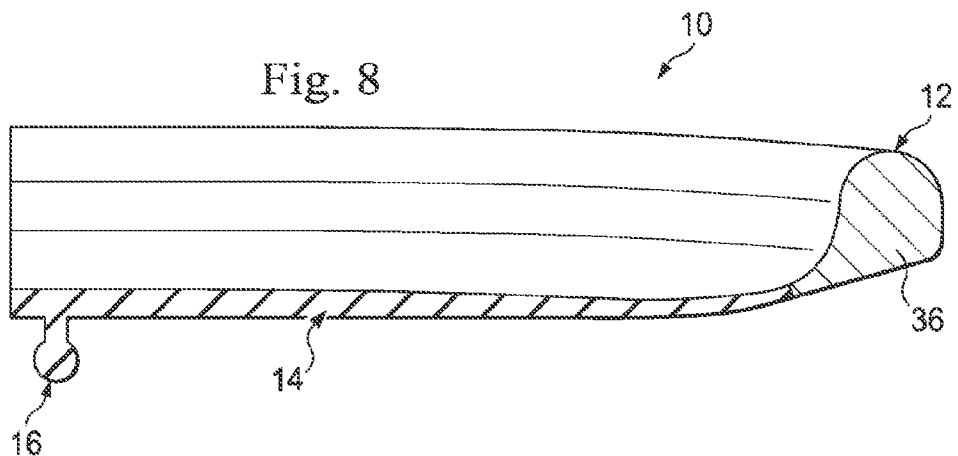
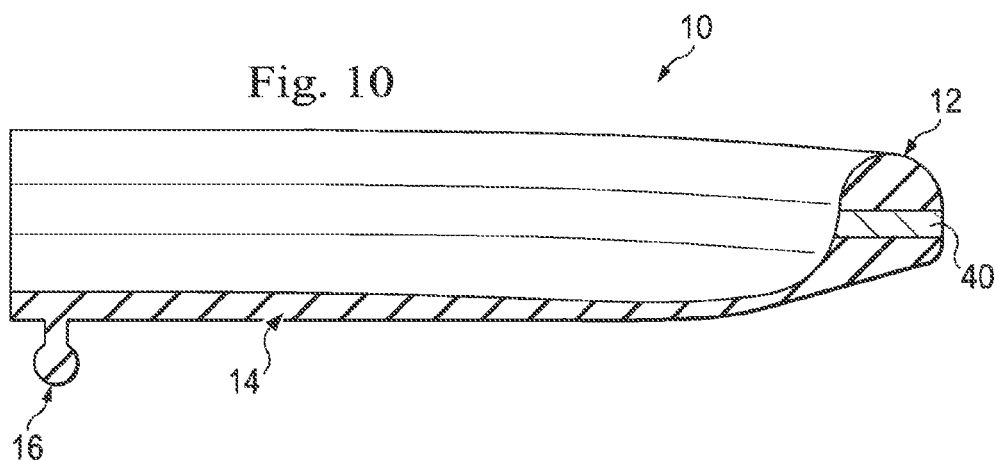
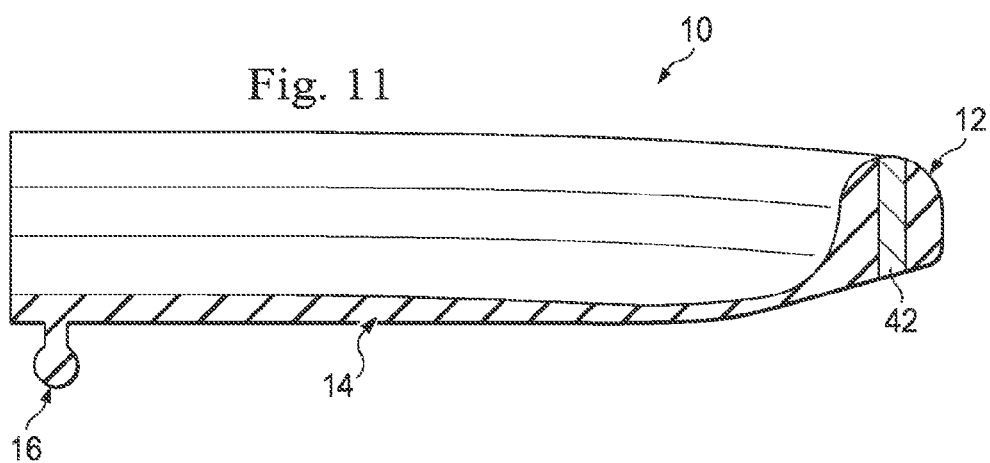

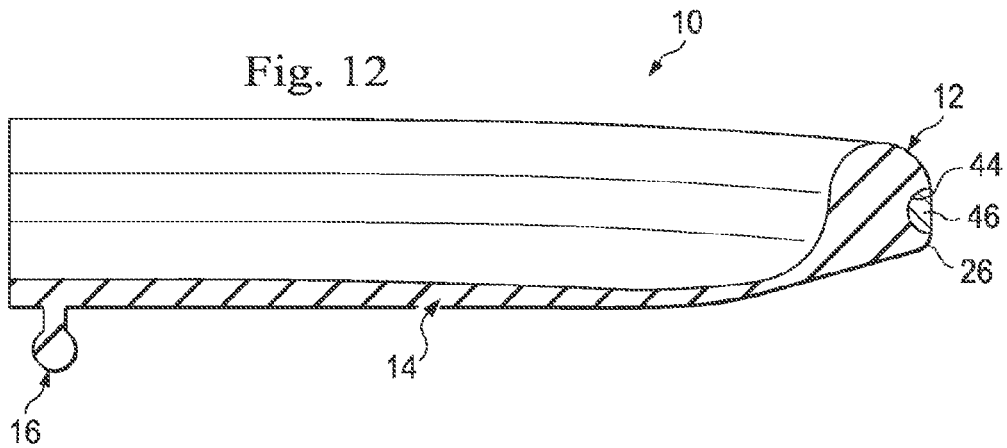
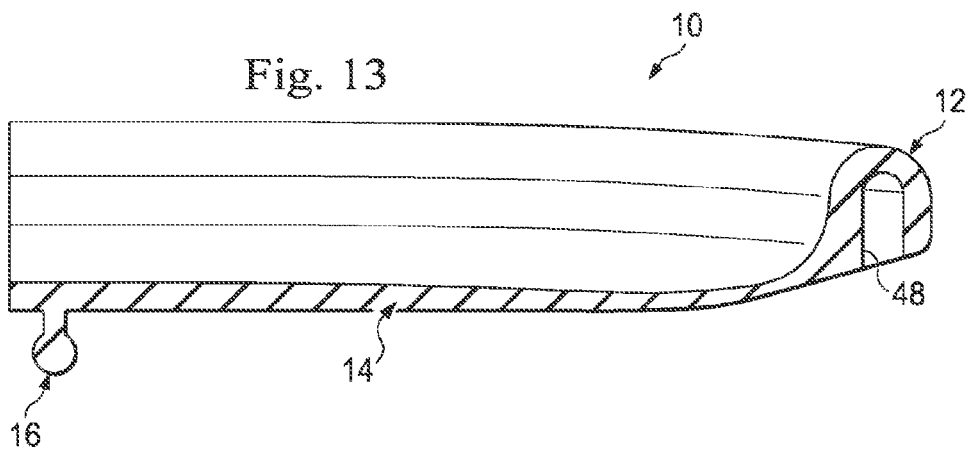
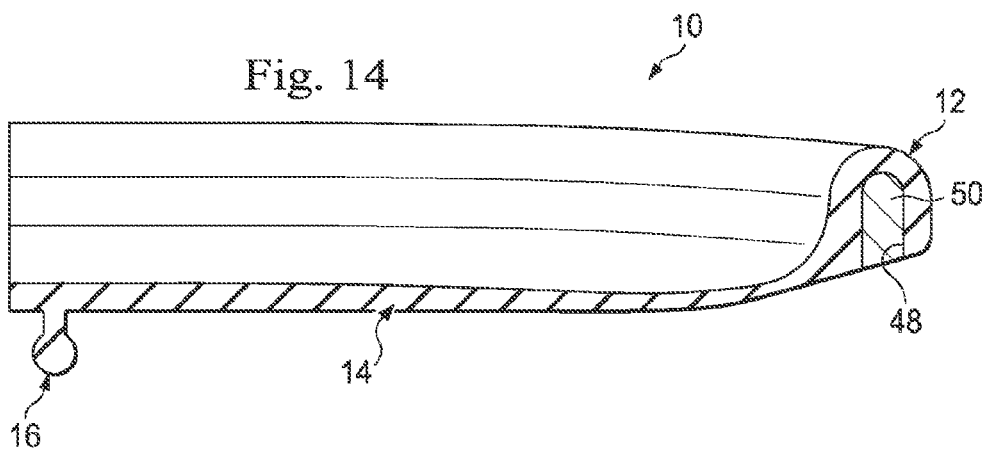

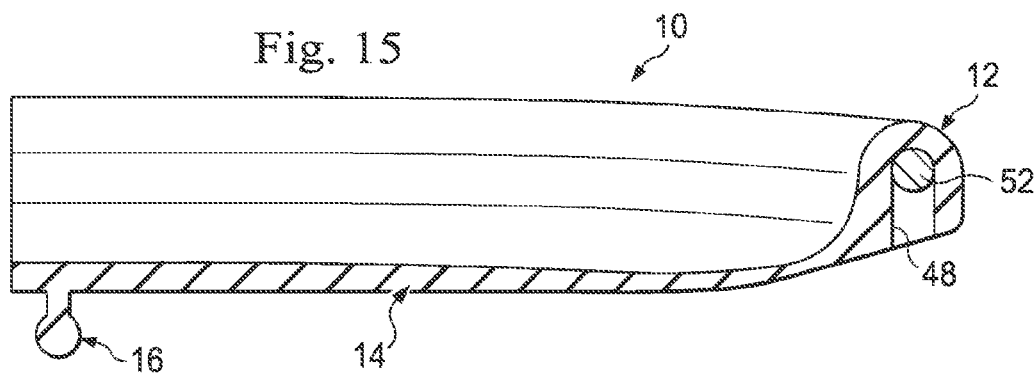
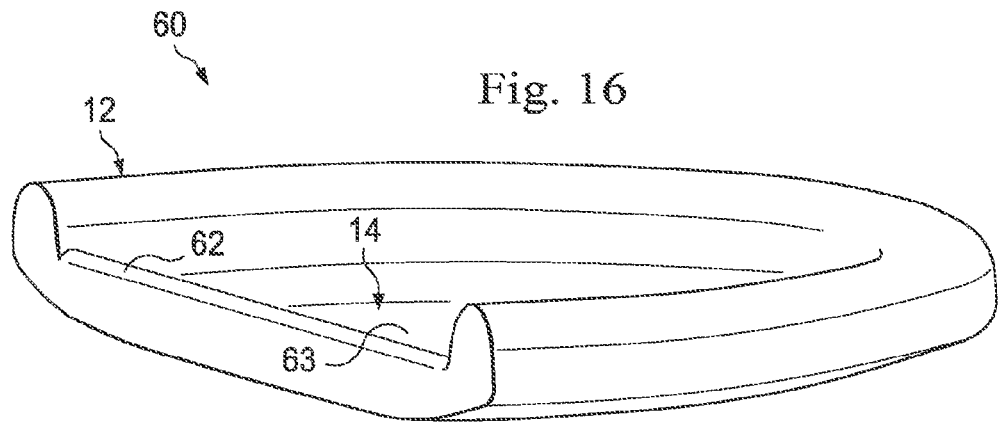

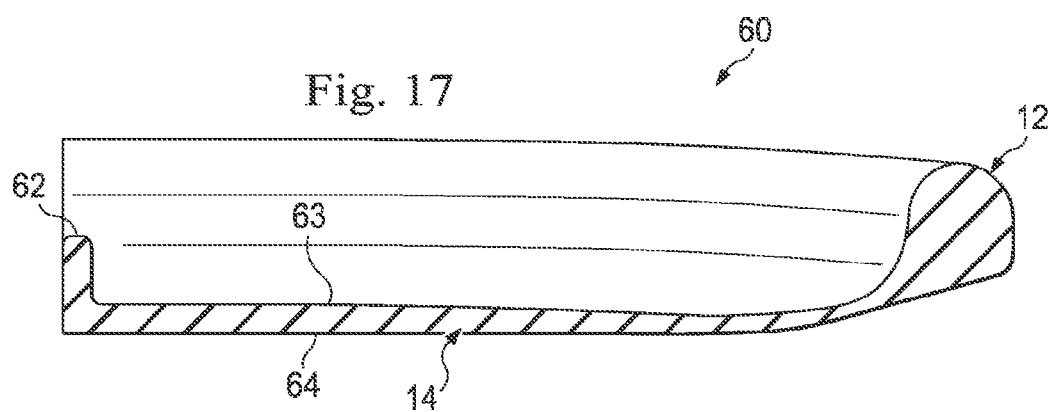
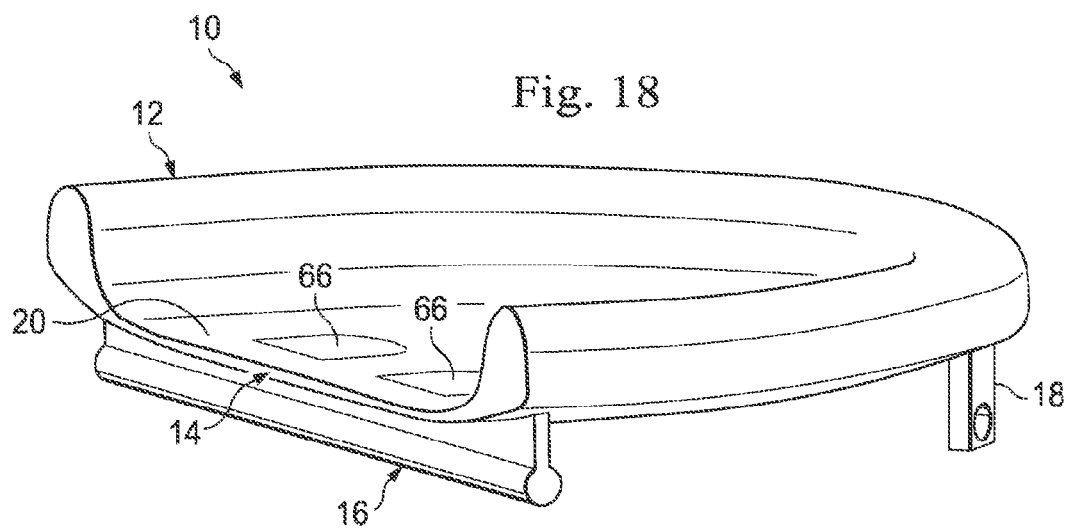

MENISCUS PROSTHETIC DEVICE

PRIORITY

This is a divisional application of U.S. patent application Ser. No. 15/134,192, filed Apr. 20, 2016, now U.S. Pat. No. 9,655,730, which is a continuation application claiming priority to U.S. patent application Ser. No. 13/481,338 filed May 25, 2012, now U.S. Pat. No. 9,320,606, which is a continuation of U.S. patent application Ser. No. 11/868,254 filed Oct. 5, 2007, now U.S. Pat. No. 8,192,491, which claims priority to U.S. Provisional Application No. 60/828,770 filed Oct. 9, 2006, each of which is hereby incorporated by reference in its entirety.

FIELD/BACKGROUND

The present disclosure generally relates to medical prosthetic devices that replace the functionality of the natural meniscus. Each knee has two menisci, a lateral meniscus and a medial meniscus. Each meniscus is a crescent-shaped fibrocartilaginous tissue attached to the tibia at an anterior and a posterior horn. Damage to the meniscus can cause debilitating pain and arthritis. In some instances the prosthetic devices of the present disclosure are configured to be surgically implanted into a knee joint to replace the natural meniscus.

SUMMARY

In one embodiment, a meniscus prosthesis is disclosed.

In another embodiment, a meniscus prosthesis is disclosed that achieves good tribology by maintaining precise contact surfaces between the meniscus, the femoral condyle cartilage, and the tibial plateau cartilage. This is accomplished through the use of a hollow-like structure that is capable of the deformation necessary to accommodate the cartilage surfaces. The prosthesis can advantageously utilize modern material technology in a configuration that, in addition to its outstanding physical characteristics, significantly reduces the need for customization and fitting of the prosthesis during the implantation procedure. The meniscus prosthesis can be manufactured in a sufficient range of sizes to fit all applications. In some embodiments, the means for mechanical fixation of the implant to the tibial platform may be integrated into the meniscus body eliminating the requirement for the meniscus to be connected to an intermediary, separate fixation means such as a bone bridge. The fixation anchor configuration can utilize a keyhole cross section geometry that provides secure position control while minimizing lateral stresses that may result from the bone screw securing techniques of prior approaches.

In another embodiment, a meniscus prosthetic device comprises a semi-ellipsoidal solid body structure having top and bottom surfaces. The top surface is concavely shaped to mate with a surgically prepared femoral condyle and the bottom surface is shaped to mate with a surgically prepared tibial plateau. The top and bottom surfaces define a shelf comprising a membrane section that extends between the interior of the semi-elliptical walls of the body structure. The thickness of the membrane section may be less than approximately 2 millimeters and the height of the semi-elliptical walls may be less than approximately 15 millimeters. The cross section of the walls of the body structure functionally duplicates the nominal cross section of the natural meniscus. A fixation anchor may be integrated into and extend from the bottom surface of the prosthetic device.

In some embodiments, the fixation anchor comprises a keel having a keyhole shaped cross section. The anchor may extend substantially parallel to the bottom surface of the prosthetic device. The anchor may be in close proximity to the edge of the shelf in some embodiments. The keel may either continuously or discontinuously extend across the width of the bottom surface. In addition, the fixation anchor may comprise one or more tabs projecting from and perpendicular to the bottom surface. In a further embodiment, the meniscus may comprise a non-biologically derived material such as a pliable polyurethane based polymer. In another implementation, the meniscus may further include a deformation control element integrated into the meniscus that may, for example, be a filament wound into a machined undercut in the lower surface. In another embodiment, the bottom surface of the meniscus may be coated with a bioactive coating applied for the purpose of encouraging the in-growth of natural tissue into the meniscus. Such in-growth may improve fixation of the replacement meniscus to the tibial plateau.

BRIEF DESCRIPTION OF DRAWINGS

Other features and advantages of the present disclosure will become apparent in the following detailed description of embodiments of the disclosure with reference to the accompanying of drawings, of which:

FIG. 3 is an alternative diagrammatic perspective view of the prosthetic device of FIGS. 1 and 2.

FIG. 4 is an alternative diagrammatic perspective view of the prosthetic device of FIGS. 1, 2, and 3.

FIG. 5 is a diagrammatic cross-sectional view of the prosthetic device of FIGS. 1, 2, 3, and 4.

FIG. 6 is a diagrammatic side view of an arrangement showing the prosthetic device of FIGS. 1, 2, 3, and 4 inserted into a surgically prepared knee joint.

FIG. 7 is a diagrammatic front view of the arrangement of FIG. 6.

FIG. 8 is a diagrammatic cross-sectional view of a prosthetic device similar to FIG. 5, but showing an alternative embodiment.

FIG. 9 is a diagrammatic cross-sectional view of a prosthetic device similar to FIGS. 5 and 8, but showing an alternative embodiment.

FIG. 10 is a diagrammatic cross-sectional view of a prosthetic device similar to FIGS. 5, 8, and 9, but showing an alternative embodiment.

FIG. 11 is a diagrammatic cross-sectional view of a prosthetic device similar to FIGS. 5, 8, 9, and 10 but showing an alternative embodiment.

FIG. 12 is a diagrammatic cross-sectional view of a prosthetic device similar to FIGS. 5, 8, 9, 10, and 11, but showing an alternative embodiment.

FIG. 13 is a diagrammatic cross-sectional view of a prosthetic device similar to FIGS. 5, 8, 9, 10, 11, and 12 but showing an alternative embodiment.

FIG. 14 is a diagrammatic cross-sectional view of the prosthetic device of FIG. 13 with an insert according to one embodiment of the present disclosure.

FIG. 15 is a diagrammatic cross-sectional view of a prosthetic device FIG. 13 with an insert similar to FIG. 14, but showing an alternative embodiment of the insert.

FIG. 16 is a diagrammatic perspective view of a prosthetic device according to another embodiment of the present disclosure.

FIG. 17 is a diagrammatic cross-sectional view of the prosthetic device of FIG. 16.

FIG. 18 is a diagrammatic perspective view of a prosthetic device according to another embodiment of the present disclosure.

DETAILED DESCRIPTION

Figure 1:
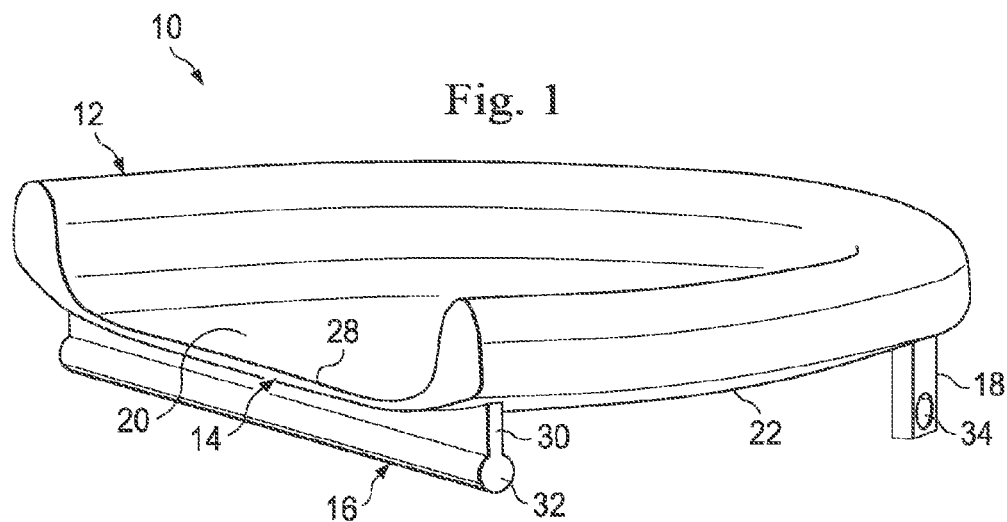
FIG. 1 is a diagrammatic perspective view of an embodiment of a prosthetic device according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Figure 2:
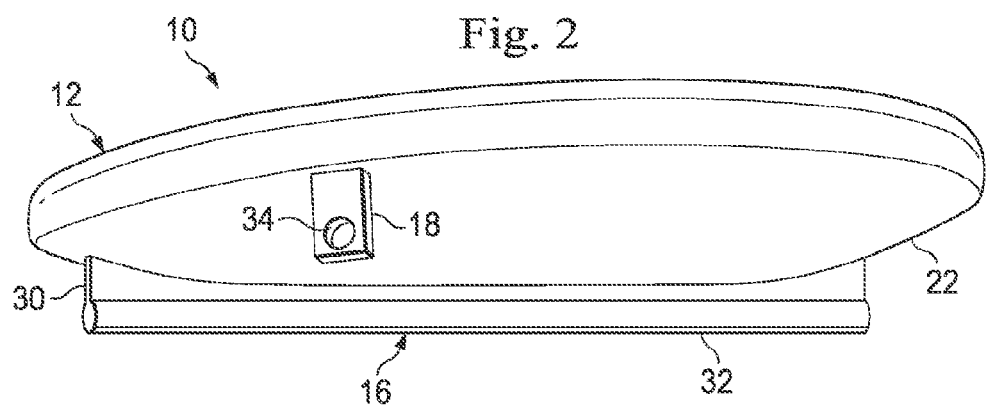
FIG. 2 is an alternative diagrammatic perspective view of the prosthetic device of FIG. 1.

Referring now to FIGS. 1, 2, 3, 4, and 5 shown therein is a prosthetic device 10 according to one aspect of the present disclosure. In particular, FIGS. 1, 2, 3, and 4 are various perspective views of the device 10. FIG. 5 is a cross-sectional view of the device 10. Generally, the prosthetic device 10 is for the replacement of a meniscus that has been damaged, ruptured, disintegrated, diseased, or is otherwise in need of replacement. For illustrative purposes, the prosthetic device 10 will be described for use with a left knee, lateral meniscus replacement. However, corresponding embodiments may be utilized for replacement of any of the other menisci, such as the left knee medial meniscus, right knee lateral meniscus, and/or right knee medial meniscus. In that regard, the position, size, shape, and/or other properties of the fixation anchor may be configured for each particular application. Similarly, the size, shape, thickness, material properties, and/or other properties of the prosthetic device may be configured for each particular application.

The prosthetic meniscus 10 comprises an outer body portion 12, a central body portion 14, a fixation member 16, and a fixation device 18. Generally, the outer body portion 12 has an increased thickness and height relative to the central body portion 14. In some instances the outer body portion 12 has a thickness between 5 mm and 15 mm. In some instances, the central body portion 14 has a thickness between 0.1 mm and 5 mm. In one particular embodiment, the outer body portion 12 has a thickness of approximately 10 mm and the central body portion 14 has a thickness of approximately 2 mm. Further, in some instances the outer body portion 12 has an increased stiffness relative to the central body portion 14. As discussed in greater detail below, this increased stiffness may be a result of different material properties, geometries, support features, and/or other mechanisms for varying the stiffness between the central body portion 14 and the outer body portion 12.

Generally, the central body portion 14 defines an upper articulation surface 20 and a lower fixation surface 22. The fixation member 16 extends from the lower fixation surface 22. The upper articulation surface 20 is bounded by the outer body portion 12 on several sides. In that regard, the outer body portion 12 comprises a rim or wall having an increased height relative to the central body portion 14 such that the central body portion is recessed with respect to the outer body portion. In the current embodiment, the outer body portion 12 defines a substantially convex upper surface 24 that tapers down in to the upper articulation surface 20 on one side and to an outer surface 26 of the prosthetic device 10 on the other side. Accordingly, the upper surface 20 of the central body portion 14 and the taper of the upper surface 24 of the outer body portion 12 define a concave recess configured for receiving a portion of the femur such as the femoral condyle. The outer body portion 12 has a semi-ellipsoidal shape in some embodiments. In one particular embodiment, the outer body portion 12 is shaped to substantially match the shape of a natural meniscus.

While the majority of the central body portion 14 is bounded by the outer body portion 12, one side of the body portion 12 defines an edge or boundary 28. In the current embodiment, the boundary 28 is a substantially planar surface having a thickness approximately equal to the thickness of the central body portion 14. In other embodiments, the boundary 28 may have an increased thickness relative to the central body portion 14 (e.g., see FIGS. 16 and 17). In some embodiments, the boundary 28 has a thickness greater than the central body portion 14, but less than the outer body portion 12. In one particular embodiment, the boundary 28 may have a thickness such that it extends above the upper surface 20 approximately one-half of the distance of the upper surface 24 of the outer body portion 12.

As noted above, the fixation member 16 extends down from the lower surface 22 of the prosthetic device 10. In the current embodiment, the fixation member 16 extends from the lower surface 22 adjacent to and substantially parallel to the boundary 28. In other embodiments, the fixation member 16 may extend from other portions of the prosthetic device 10 and/or in other directions, including directions substantially perpendicular to the boundary 28 and/or oblique to the boundary 28. Alternative positioning and orientations of the fixation member 16 are used to accommodate alternative surgical approaches, patient specific anatomical attributes, meniscus specific orientations, physician preference, and/or other factors.

In the current embodiment, the fixation member 16 comprises a keel structure having a first portion 30 extending directly from the lower surface 22 and a second portion 32 extending from the first portion 30. The second portion 32 has an increased profile or thickness relative to the first portion 30. In the current embodiment, the fixation member 16 has a keyhole cross section that can engage a complementary keyhole shaped groove that has been surgically incised a portion of the tibia, such as the tibia plateau, according to a keyhole surgical approach. In that regard, the fixation member 16 is configured to engage an opening extending substantially in a direction from the anterior to the posterior of the tibia. In other embodiments, the fixation member 16 may have other structural geometries to encourage engagement with the tibia. In one particular embodiment, the fixation member 16 comprises a dovetail configured to engage a dovetailed groove prepared in the tibia.

The fixation member 16 is manufactured as an integral part of the prosthetic device in some embodiments. In that regard, the fixation member 16 may be molded simultaneously with the other portions of the prosthetic device 10 and/or permanently attached to the other portions of the prosthetic device. Implementing the fixation member 16 as an integral component of the prosthetic device 10 provides several distinct advantages. First, the configuration and dimensions of the fixation member 16 are precisely controlled prior to the surgical procedure and may be maintained even for different size prosthetic devices 10. Accordingly, a single size of standardized surgical tools, including bores, rasps and guides, etc., may be employed for the implantation of any size prosthetic device 10. This results in a more precise engagement and mating between the prosthetic device 10 and the tibia, which improves the fixation properties and overall performance of the prosthetic device. Second, by implementing the fixation member 16 as an integrated section of the overall prosthetic device 10, the possibility of separation of the fixation member 16 from the other portions of the prosthetic device 10 is virtually eliminated. Third, the keyhole and/or dovetail configurations of the fixation member 16 do not require the use of bone screws or other means to tighten or secure the fixation member 16 to the tibia. Accordingly, the integral fixation member 16 minimizes or eliminates the need to customize the fixation member, thereby reducing the time required to perform the implantation procedure.

In some embodiments, a fixation device 18 is utilized in combination with the fixation member 16 to secure the prosthetic device 10 to the tibia. It should be noted, however, that in other embodiments, the fixation member 16 is the sole fixation means utilized to secure the prosthetic device 10 to the tibia. The fixation device 18 extends from the bottom surface 22. As shown, in some embodiments the fixation device 18 extends substantially perpendicularly to the bottom surface 22. The fixation device 18 is utilized to provide further fixation of the prosthetic device 10 to the tibia. In that regard, in the current embodiment the fixation device 18 includes an opening 34 for receiving a fixation member. The fixation member may be a bone screw, staple, or other device configured to secure the prosthetic device 2 to the tibia through the opening 34. In one particular embodiment, the fixation device 18 may be fastened to the tibia by means of a bone screw extending through the opening and securely engaging the tibia.

When the prosthetic device 10 is implanted and secured to the tibia, the central body portion 14 bounded by the outer body portion 12 serves to isolate the femoral condyle from the tibial plateau when implanted into a patient. In that regard, the outer body portion 12 serves to limit the movement of the femoral condyle relative to the prosthetic device. In particular, in the current embodiment the outer body portion 12 prevents the portion of the femur movingly engaged with the prosthetic device 10 from moving laterally beyond outer body portion. In other embodiments, the outer body portion 12 limits movement of the femur relative to the prosthetic device 10 in the medial direction. Further, the prosthetic device 10 provides shock absorption and a desirable tribology between the femur and tibia thereby attributing to the overall therapeutic value of the prosthesic device.

The prosthetic device 10 may be manufactured in various sizes, so that any given application can be satisfied by a "stock" unit. Accordingly, a surgeon could, during an implantation procedure, select a correctly sized device from the selection of stock units. Alternatively, in another embodiment, a replacement meniscus could be custom manufactured for a particular patient utilizing characteristics determined by medical imaging techniques, such as MRI, coupled with computer aided manufacturing (CAM) techniques.

In some embodiments, the bottom surface 22 of the prosthetic device 10 is coated with a bioactive coating to encourage the in-growth of natural tissue to further improve fixation of the prosthetic device to the tibial plateau. In some embodiments, the coating is formed by grit blasting or spraying the bottom surface 22. The bioactive coating may be any suitable material for encouraging tissue growth and, in some embodiment, may be specifically adapted for promoting bone growth between the tibia and the prosthetic device 10.

Referring generally to FIGS. 8-15, in some embodiments the outer body portion 12 of the prosthetic device 10 includes a deformation control element to limit the deformation of the outer body portion. As will be described in greater detail with respect to the specific embodiments shown in FIGS. 8-15, the deformation control element may be a material property, a structural property, an additional component, and/or combinations thereof. It should be noted that the various deformation control elements described herein may be combined to further limit or define the amount of deformation of the outer body portion 12.

Referring more particularly to FIG. 8, shown therein is a cross-sectional view of the prosthetic device 10 wherein the outer body portion 12 is comprised of a reinforced material relative to the central body portion 14. For example, in one embodiment the outer body portion 12 includes carbon fibers providing additional strength and limiting the flexibility of the outer body portion. In some embodiments the carbon fibers are injected prior to the curing of the outer body portion 12. In other embodiments, the outer body portion 12 is formed or molded around the carbon fibers. In other embodiments, other additives are utilized to reinforce the material of the outer body portion 12. The particular additives that are used depend upon the material(s) used for forming the outer body portion 12. As shown in FIG. 8, in the current embodiment the entire outer body portion 12 is formed from a substantially uniform materials and/or the additives are equally distributed throughout the outer body portion. However, in other embodiments the deformation control element may comprise only a portion of the outer body portion 12. In that regard, the deformation control element may extend along only a portion of the outer body portion 12, the deformation control element may be positioned within a particular portion of the outer body portion, and/or combinations thereof.

For example, referring more particularly to FIG. 9, shown therein is a cross-sectional view of the prosthetic device 10 wherein the outer body portion 12 includes a wire, cable, or filament 38 extending therethrough. The filament increases the stiffness of the outer body portion 12 to limit the flexibility and/or deformity. In some embodiments, the filament 38 comprises a carbon fiber. In other embodiments, the filament 38 comprises a metal, polymer, or other material having an increased hardness and/or stiffness relative to the material comprising the central body portion 14. In some embodiments, the outer body portion 12 is formed around the filament 38. In other embodiments, the filament 38 is inserted into the outer body portion 12 prior to curing of the prosthetic device 12. In some embodiments, the filament 38 is inserted into an opening in the body portion 12 and then additional material is inserted into the opening to close the opening and secure the filament therein. In the current embodiment, the filament 38 is shown having a substantially circular or cylindrical cross-section. However, in other embodiments the filament 38 may have other geometrical cross-sections and/or varying cross-sections along its length. The cross-section(s) of the filament 38 are configured to provide the desired stiffness and deformation properties to the outer body portion 12.

Further in the current embodiment, the outer body portion 12 has a total thickness or height $H_1$, the filament 38 is positioned a distance $H_2$ from the peak of the upper surface

24, and the filament has a height $H_3$. In some embodiments, the total thickness $H_1$ of the outer body portion 12 is between 5 mm and 15 mm. In some embodiments, the thickness $H_3$ of the filament 38 is between ¼ and ½ of the total thickness $H_1$ of the outer body portion 12. The distance $H_2$ from the peak of the upper surface 24 to the filament 38 varies from 0 (i.e., the filament 38 is positioned at the top of the outer body portion 12) to ¾ of the total thickness $H_1$ (i.e., the filament is positioned at the bottom of the outer body portion). In that regard, in some embodiments the filament 38 may engaged a recess in the upper surface 24 or the lower surface of the outer body portion 12 configured to receive the filament 38. In one particular embodiment, the total thickness $H_1$ is approximately 10 mm, the distance $H_2$ is approximately 3.3 mm, and the thickness $H_3$ is approximately 3.3 mm.

Similarly, in the current embodiment the outer body portion 12 has a total thickness or width $W_1$, the filament 38 is positioned a distance $W_2$ from the outer surface 26, and the filament has a width $W_3$. In some embodiments, the total width $W_1$ of the outer body portion 12 is between 5 mm and 15 mm. In some embodiments, the width $H_3$ of the filament 38 is between ¼ and ½ of the total width $W_1$ of the outer body portion 12. The distance $W_2$ from the peak of the upper surface 24 to the filament 38 varies from 0 (i.e., the filament 38 is positioned at the very inside of the outer body portion 12) to ¾ of the total width $W_1$ (i.e., the filament is positioned at the outside of the outer body portion). In that regard, in some embodiments the filament 38 may engaged a recess in the outer surface 26 or the inner surface of the outer body portion 12 configured to receive the filament 38. In one particular embodiment, the total width $W_1$ is approximately 10 mm, the distance $W_2$ is approximately 3.3 mm, and the width $W_3$ is approximately 3.3 mm. In some embodiments, the outer body portion 12 may include multiple filaments 38 positioned therein. In that regard, the multiple filaments 38 may be spaced equally about the outer body portion 12 and/or grouped into specific areas of the outer body portion.

Further, in the illustrated embodiment the fixation member 16 includes a filament 39 extending therethrough. The filament 39 increases the stiffness of the fixation member 16. In the current embodiment, the filament 39 extends substantially along the length of the fixation member 16 through portion 32. In other embodiments, the fixation member 16 may include other features that increase the stiffness of the fixation member. In particular, the fixation member 16 may include features similar to those described with respect to the deformation control elements of the outer body portion 12.

Referring now to FIG. 10, shown therein is a cross-sectional view of the prosthetic device 10 wherein the outer body portion 12 includes area 40 of increased stiffness and/or hardness. In the current embodiment the area 40 extends substantially across the entire width of the outer body portion 12. The area 40 may comprise a different material from the rest of the outer body portion, the same material as the rest of the outer body portion with additives, and/or an insert piece configured to be secured within the outer body portion. As mentioned with respect to the other deformation control elements, the position, size, and shape of the area 40 is configured to achieve the desired deformation properties for the outer body portion 12. For example, referring to FIG. 11, shown therein is a cross-sectional view of the prosthetic device 10 wherein the outer body portion 12 includes an area 42 of increased stiffness and/or hardness extending substantially along the entire thickness or height of the outer body portion.

Referring now to FIG. 12, shown therein is a cross-sectional view of the prosthetic device 10 wherein the outer body portion 12 includes a recess 44 for receiving a component 46 for defining the deformation properties of the outer body portion. For example, in some instances the component 46 may be a wire, cable, or filament similar to the filament 38 described above. In other instances, the component 46 may be a material that is injected or otherwise introduced into the recess 44 in the outer surface 26. Generally, the size of the recess 44 and the properties of the component 46 are tailored to achieve the desired deformation properties of the outer body portion 12. In some embodiments, the recess 44 comprises between ⅛ and ⅔ of the height of the outer body portion 12 and between ⅛ and ⅔ of the width of the outer body portion. In many embodiments, the component 46 substantially fills the entire recess 44. However, in some embodiments the component 46 is sized such that it fills only a portion of the recess 44. In such embodiments, the remaining portion of the recess 44 may remain vacant or be filled with another material. In some embodiments, the component 46 is secured in the recess 44 by the introduction of additional material into the open space remaining in the recess.

Referring now to FIGS. 13 and 14, shown therein is a cross-sectional view of the prosthetic device 10 wherein the outer body portion 12 includes an undercut 48 extending upward from the bottom surface of the outer body portion. In some instances the undercut 48 is configured to receive a component 50 for increasing the stiffness and limiting the deformation of the outer body portion 12. For example, in some instances the component 50 may be a wire, cable, or filament similar to the filament 38 described above. In other instances, the component 50 may be a material that is injected or otherwise introduced into the recess 48 in the outer surface 26. Generally, the size of the recess 48 and the properties of the component 50 are selected to achieve the desired deformation properties of the outer body portion 12. In some embodiments, the recess 48 comprises between ⅛ and ⅞ of the height of the outer body portion 12 and between ⅛ and ⅞ of the width of the outer body portion. In many embodiments, the component 50 substantially fills the entire recess 48, as shown in FIG. 14. However, in some embodiments a component 52 is sized such that it fills only a portion of the recess 48, as shown in FIG. 15. In such embodiments, the remaining portion of the recess 44 may remain vacant—as shown in FIG. 15—or the remaining open portion may be filled with another material or component. In some embodiments, the component 52 is secured in the recess 48 by the introduction of additional material into the open space remaining in the recess.

Referring now to FIGS. 16 and 17, shown therein is a prosthetic device 60 according to another embodiment of the present disclosure. In some instances, the prosthetic device 60 is substantially similar to the prosthetic device 10 described above. Accordingly, similar reference numerals may be utilized and the description limited for particular aspects of the prosthetic device 60. However, it should be noted that the prosthetic device 60 does not include a fixation member 16 or a fixation device 18 as described with respect to the prosthetic device 10. Rather, the prosthetic device 60 is configured to be implanted without rigid fixation to either the femur or tibia. In this regard, the prosthetic device 60 may be implanted into a patient without causing permanent damage to the patient's tibia or other bone structure(s) engaged by the prosthetic device. Accordingly, the prosthetic device 60 may be implanted in an attempt to alleviate the patient's knee problems while avoiding permanent destruction of the patient's anatomy, such as cutting or reaming a large opening in the tibia. more invasive procedures.

To this end, the prosthetic device 60 includes a boundary 62 extending between the ends of the outer body portion 12 having an increased height relative to the central body portion 14. In that regard, the boundary 62 extends substantially above an upper surface 63 of the central body portion 14. Accordingly, the outer body portion 12 and the boundary 62 completely surround the central body portion 14. Accordingly, when positioned between the femur and tibia the outer body portion 12 and the boundary 62 define the outer limits of movement for the femur relative to the prosthetic device 60. That is, the increased height of the outer body portion 12 and the boundary 62 along with the contact pressure on the prosthetic device 60 from being positioned between the femur and the tibia prevents the femur from escaping the cavity defined by the outer body portion 12 and the boundary 62. In some embodiments, the boundary 62 has a thickness that is between ¼ and ¾ the total thickness or height of the outer body portion 12. In one particular embodiment, the boundary 62 has thickness such that it extends above the upper surface 63 approximately one-half of the distance of the upper surface 24 of the outer body portion 12.

Further, the upper surface 63 and the lower surface 64 are both articulating bearing surfaces in the current embodiment. In particular, the upper and lower surfaces 63, 64 are configured to movingly engage with the femur and tibia, respectively. In that regard, the prosthetic device 60 can translate and rotate with respect to the femur and/or tibia. Translation is possible in both the anterior-posterior and medial-lateral directions. In some embodiments, the upper surface 63 includes both a vertical and a horizontal bearing component. To that end, in some embodiments the upper surface 63 comprises a concave surface that defines the vertical and horizontal bearing components. Similarly, in some embodiments the lower surface 64 includes both a vertical and horizontal bearing component. In particular, in some embodiments the lower surface 64 comprises a convex surface. In other embodiments, the lower surface 64 comprises only a vertical bearing component and is substantially planar. In such embodiments, the tibia may be prepared to mate with the substantially planar lower surface. In some embodiments, the upper surface 63 and/or the lower surface 64 are shaped such that the prosthetic device 10 is biased towards a neutral position in the knee. For example, the arcuate profiles of the upper surface 63 and/or the lower surface 64 are shaped such that the interaction between the surfaces and the bone encourages the bone to a particular orientation relative to the surfaces.

Referring to FIG. 18, in some embodiments the prosthetic device 10 includes one or more recesses 66 in the upper surface 20 that provide for the accumulation of synovial fluid. In some embodiments, the recesses 66 are positioned at the most prevalent contact points of the femur with the upper surface 20. In such embodiments, the synovial fluid lubricates the upper articulation surface 20 of the prosthetic device. The recesses 66 may have various shapes within the upper surface 20. In that regard, the recesses 66 may comprises a sloping depression that creates a concave recess in some embodiments. The concave recess may comprises a substantially circular profile, an elongated profile, an irregular shape, and/or combinations thereof. In the current embodiment, the recesses 66 are shown as comprising a D-shaped profiles spaced equally about a midline of the prosthetic device 10. However, this depiction is not to be limiting as many shapes, sizes, and transitions may be utilized for the recesses 66. In other embodiments, the prosthetic device 10 includes a greater or fewer number of recesses 66. In some embodiments, the prosthetic device 10 does not include any recesses in the upper surface 20.

In some instances, the femoral condyle may be surgically prepared to permit near-normal knee joint flexion after implantation. Similarly, the tibial plateau may be surgically prepared to fixedly engage with the prosthetic devices.

A variety of materials are suitable for use in making the prosthetic meniscus. Medical grade polyurethane based materials especially suitable for use in the embodiments described include, but are not limited to the following:

Bionate®, manufactured by POLYMER TECHNOLOGY GROUP PTG, a polycarbonate-urethane is among the most extensively tested biomaterials ever developed. Carbonate linkages adjacent to hydrocarbon groups give this family of materials oxidative stability, making these polymers attractive in applications where oxidation is a potential mode of degradation, such as in pacemaker leads, ventricular assist devices, catheters, stents, and many other biomedical devices. Polycarbonate urethanes were the first biomedical polyurethanes promoted for their biostability. Bionate® polycarbonate-urethane is a thermoplastic elastomer formed as the reaction product of a hydroxyl terminated polycarbonate, an aromatic diisocyanate, and a low molecular weight glycol used as a chain extender. The results of extensive testing encompassing Histology, Carcinogenicity, Biostability, and Tripartite Biocompatibility Guidance for Medical Devices verifies the cost effective material's biocompatibility.

Another group of potentially suitable materials are copilymers of silicone with poplyurethanes as exemplified by PurSil™, a Silicone Polyether Urethane and CarboSil™, a Silicone Polycarbonate Urethane. Silicones have long been known to be biostable and biocompatible in most implants, and also frequently have the low hardness and loq modulus useful for many device applications. Conventional silicone elastomers can have very high ultimate elongations, but only low to moderate tensile strengths. Consequently, the toughness of most biomedical silicone elastomers is not particularly high. Another disadvantage of conventional silicone elastomers in device manufacturing is the need for cross-linking to develop useful properties. Once cross-linked, the resulting thermoset silicone cannot be redissolved or remelted. In contrast, conventional polyurethance elastomers are generally thermoplastic with excellent physical properties. Thermoplastic urethane elastomers (TPUs) combine high elongation and high tensile strength to form tough, albeit fairly high-modulud elastomers. Aromatic polyether TPUs can hica excellent flex life, tensile strength exceeding 5000 psi, and ultimate elongations greater than 700 percent. The are often used for continuously flexing, chronic implants such as ventricular-assist devices, intraaortic balloons, and artificial heart components. TPUs can easily be processed by melting or dissolving the polymer to fabricate it into useful shapes.

The prospect of combining the biocompatibility and biostability of conventional silicone elastomers with the processability and toughness of TPUs is an attractive approach to what would appear to be a nearly ideal biomaterial. For instance, it has been reported that silicone acts synergistically with both polycarbonate- and polyether-based polyurethanes to improve in vivo and in vitro stability. In polycarbonate-based polyurethanes, silicone copolymerization has been shown to reduce hydrolytic degradation of the carbonate linkage, whereas in polyether urethanes, the covalently bonded silicone seems to protect the polyether soft segment from oxidative degradation in vivo.

POLYMER TECHNOLOGY GROUP PTG synthesized and patented silicone-polyurethane copolymers by combining two previously reported methods: copolymerization of silicone (PSX) together with organic (non-silicone) soft segments into the polymer backbone, and the use of surface-modifying end groups to terminate the copolymer chains. Proprietary synthesis methods make high-volume manufacturing possible.

Other potentially applicable materials include PurSil™ silicone-polyether-urethane and CarboSil™ silicone-polycarbonate-urethane which are true thermoplastic copolymers containing silicone in the soft segment. These high-strength thermoplastic elastomers are prepared through a multi-step bulk synthesis where polydimethylsiloxane (PSX) is incorporated into the polymer soft segment with polytetramethyleneoxide (PTMO) (PurSil) or an aliphatic, hydroxyl-terminiated polycarbonate (CarboSil). The hard segment consists of an aromatic diisocyanate, MDI, with low molecular weight glycol chain extender. The copolymer chains are then terminated with silicone (or other) Surface-Modifying End Groups™ Aliphatic (AL) versions of these materials, with a hard segment synthesized from an aliphatic diisocyanate are also available.

Many of these silicone urethanes demonstrate previously unavailable combinations of physical properties. For example, aromatic silicone polyetherurethanes have a higher modulus at a given shore hardness than conventional polyether urethanes—the higher the silicone content, the higher the modulus (see PurSil Properties). Conversely, the aliphatic silicone polyetherurethanes have a very low modulus and a high ultimate elongation typical of silicone homopolymers or even natural rubber (see PurSil AL Prperties). This makes them very attractive as high-performance substitutes for conventional cross-linked silicone rubber. In both the PTMO and PC families, certain polymers have tensile strengths three to five times higher than conventional silicone biomaterials.

Further examples of suitable materials include Surface Modifying End Groups™ (SMEs) which are surface-active oligomers covalently conded to the base polymer during synthesis. SMEs—which include silicone (S), sulfonate (SO), fluorocarbon (F), polyethylene oxide (P), and hydrocarbon (H) groups—control surface chemistry without compromising the bulk properties of the polymer. The result is key surface properties, such as thromboresistance, biostability, and abrasion resistance, are permanently enhanced without additional post-fabrication treatments or topical coatings. This patented technology is applicable to a wide range of PTG's polymers.

SMEs provide a series of (biomedical) base polymers that can achieve a desired surface chemistry without the use of additives. Polyurethanes prepared according to PTG's development process couple endgroups to the backbone polymer during synthesis via a terminal isocyanate group, not a hard segment. The added mobility of endgroups relative to the backbone is though to facilitate the formation of uniform overlayers by the surface-active (end) blocks. The use of the surface active endgroups leaves the original polymer backbone intact so the polymer retains strength and processability. The fact that essentially all polymers chains carry the surface-modifying moiety eliminates many of the potential problems associated with additives.

The SME approach also allows the incorporation of mixed endgroups into a single polymer. For example, the combination of hydrophobic and hydrophilic endgroups gives the polymers amphipathic characteristics in which the hydrophobic versus hydrophilic balance may be easily controlled.

Other suitable materials, manufactured by CARDIOTECH CTE, include ChronoFlex® And Hydrothane™.

The ChronoFlex®, polycarbonate aromatic polyurethanes, family of medical-grade segmented biodurable polyurethane elastomers have been specifically developed by CardioTech International to overcome the in vivo formation of stress-induced microfissures.

HydroThane™, hydrophilic thermoplastic polyurethanes, is a family of super-absorbent, thermoplastic, polyurethane hydrogels ranging in water content from 5 to 25% by weight. HydroThane™ is offered as a clear resin in durometer hardness of 80A and 93 Shore A. The outstanding characteristic of this family of materials is the ability to rapidly absorb water, high tensile strength, and high elongation. The result is a polymer having some lubricious characteristics, as well as being inherently bacterial resistant due to their exceptionally high water content at the surface. HydroThane™ hydrophilic polyurethane resins are thermoplastic hydrogels, and can be extruded or molded by conventional means. Traditional hydrogels on the other hand are thermosets and difficult to process.

Additional suitable materials manufactured by THERMEDICS include Tecothante® (aromatic polyether-based polyurethane), Carbothane® (aliphatic polycarbonate-based polyurethane), Tecophilic® (high moisture absorption aliphatic polyether-based polyurethane) and Tecoplast® (aromatic polyether-based polyurethane). Tecothane® is a family of aromatic, polyether-based TPU's available over a wide range of durometers, colors, and radiopacifiers. One can expect Tecothane resins to exhibit improved solvent resistance and biostability when compared with Tecoflex resins of equal durometers. Carbothane® is a family of aliphatic, polycarbonate-based TPU's available over a wide range of durometers, colors and radiopacifiers. This type of TPU has been reported to exhibit excellent oxidative stability, a property which may equate to excellent long-term biostability. This family, like Tecoflex, is easy to process and does not yellow upon aging. Tecophilic® is a family of aliphatic, polyether-based TPU's which have been specially formulated to absorb equilibrium water contents of up to 150% of the weight of dry resin.

Polyurethanes are designated aromatic or aliphatic on the basis of the chemical nature of the diisocyanate component in the formulation. Tecoflex, Tecophilic and Carbothane resins are manufactured using the aliphatic compound, hydrogenated methylene diisocyanate (HMDI). Tecothane and Tecoplast resins use the aromatic compound methylene diisocyanate (MDI). Tecoflex® is a family of aliphatic, polyether-based TPU's. These resins are easy to process and do not yellow upon aging. Solution grade versions are candidates to replace latex. All formulations, with the exception of Carbothane, are formulated using plytetramethylene ether glycol (PTMEG) and 1,4 butanediol chain extender. Carbothane is specifically formulated with a polycarbonate diol (PCDO). These materials represent the major chemical composition differences among the various families. Aromatic and aliphatic polyurethanes share similar properties that make them outstanding materials for use in medical devices. In general, there is not much difference between medical grade aliphatic and aromatic polyurethanes with regard to the following chemical, mechanical and biological properties: high tensile strength (4,000 to 10,000 psi); high ultimate elongation (250 to 700%); wide range durometer (72 Shore A to 84 Shore D); good biocompatibility; high abrasion resistance; good hydrolytic stability; can be sterilized with ethylene oxide and gamma irradiation; retention of elastomeric properties at low temperature; good melt processing characteristics for extrusion, injection molding, etc.

With such an impressive array of desirable features, it is no wonder that both aliphatic and aromatic polyurethanes have become increasingly the material of choice in the design of medical grade components. There are, however, distinct differences between these tow families of polyurethane that could dictate the selection of one over the other for a particular application:

In their natural states, both aromatic and aliphatic polyurethanes are clear to very light yellow in color. Aromatics, however, can turn dark yellow to amber as a result of melt processing or sterilization, or even with age. Although the primary objection to the discoloration of aromatic clear tubing or injection molded parts is aesthetic; the yellowing, which is caused by the formation of a chromophore in the NMI portion of the polymer, does not appear to affect other physical properties of the material. Radiopaque grades of Tecothane also exhibit some discoloration during melt processing or sterilization. However, both standard and custom compounded radiopaque grades of Tecothane have been specifically formulated to minimize this discoloration.

Aromatic polyurethanes exhibit better resistance to organic solvents and oils than do aliphatics—especially as compared with low durometer (80 to 85 Shore A) aliphatic, where prolonged contact can lead to swelling of the polymer and short-term contact can lead to surface tackiness. While these effects become less noticeable at higher durometers, aromatics exhibit little or no sensitivity upon exposure to the common organic solvents used in the health care industry.

Both aliphatic and aromatic poly-ether based polyuretanes soften considerably within minutes of insertion in the body. Many device manufacturers promote this feature of the urethane products because of patient comfort advantage as well as the reduced risk of vascular trauma. However, this softening effect is less pronounced with aromatic resins than with aliphatic resins.

Tecothane, Tecoplast and Carbothane melt at temperatures considerably higher than Tecoflex and Tecophilic. Therefore, processing by either extrusion of injection molding puts more heat history into products manufactured from Tecothane, Tecoplast and Carbothane. For example, Tecoflex EG-80A and EG-60D resins mold at nozzle remperatures of approximately 310 degrees F. and 340 degrees F. respectively while Tecothane and Carbothane products of equivalent durometers mold at nozzle temperatures in the range of 380 degrees F. and 435 degrees F.

Additional materials of interest include Tecogel, a new member to the Tecophilic family, a hydrogel that can be formulated to absorb equilibrium water contents between 500% to 2000% of the weight of dry resin, and Tecoplast®, a family of aromatic, polyether-based TPU's formulated to produce rugged injection molded components exhibiting high durometers and heat deflection temperatures.

Additional potentially suitable materials include four families of polyurethanes, named Elast-Eon™, which are available from AorTech Biomaterials.

Elast-Eon™ 1, a Polyhexamethylene oxide (PFMO), aromatic polyurethane, is an improvement on conventional polyurethane in that it has a reduced number of the susceptible chemical groups. Elast-Eon™2, a Siloxane based macrodiol, aromatic polyurethane, incorporates siloxane unto the soft segment. Elast-Eon™3, a Siloxane based macrodiol, modified hard segment, aromatic polyurethane, is a variation of Elast-Eon™2 with further enhanced flexibility due to incorporation of siloxane into the hard segment. Elast-Eon™4 is a modified aromatic hard segment polyurethane.

Bayer Corporation also produces candidate materials. Texin 4210 and Texin 4215 are thermoplastic polyurethane/polycarbonate blends for injection molding and extrusion. Texin 5250, 5286 and 5290 are aromatic polyether-based medical grade materials with Shore D hardness of approximately 50, 86, and 90 respectively for injection molding and extrusion. They each comply with 21 CFR 177.1680 and 177.2600.

It should be appreciated that the devices described hereinabove, while preferably formed by injection molding of polyurethane, may also be formed by any suitable manufacturing method and may be formed of any suitable medical grade elastomers. It is further appreciated that any of the following manufacturing methods may be utilized: injection molding including inserting inserts, compression molding including inserting inserts, injection-compression molding including inserting inserts, compression molding of prefabricated elements pre-formed by any of the above methods including inserting inserts, spraying including inserting inserts, dipping including inserting inserts, machining from stocks or rods, machining from prefabricated elements including inserting inserts.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

While the present disclosure has been particularly shown and described with reference to particular embodiments, it will be fully appreciated that variations of the above-disclosed and other features and functions, or alternatives thereof, may be desirably combined into many other different systems or applications. Also that various presently unforeseen or unanticipated alternatives, modifications, variations of improvements therein may be subsequently made by those skilled in the art which are also intended to be encompassed by the following claims.

What is claimed is:
1. A method of implanting a meniscus prosthetic device, the method comprising:
   inserting the meniscus prosthetic device into a space between the femur and the tibia, wherein the meniscus prosthetic device comprises:
      a central body portion comprising a flexible polymeric material, the central body portion having an upper articulating bearing surface and a lower articulating bearing surface; and
      a perimeter completely surrounding the central body portion and having an increased thickness and an increased stiffness with respect to the central body portion, wherein the perimeter comprises a filament extending therethrough and providing the increased stiffness of the perimeter, wherein the filament is positioned superiorly relative to the upper articulating bearing surface; and implanting the meniscus prosthetic device within the space without rigidly affixing the meniscus prosthetic device to the femur or the tibia such that the meniscus prosthetic device is translatable in the anterior-posterior direction and the medial-lateral direction, wherein the perimeter is configured to limit movement of the femoral condyle with respect to the upper articulating bearing surface of the central body portion, wherein the upper articulating bearing surface is in moving engagement with the femoral condyle and the lower articulating bearing surface is in moving engagement with the tibial plateau.

2. The method of claim 1, wherein the implanting the meniscus prosthetic device does not include removing any portion of the tibial plateau.

3. The method of claim 1, wherein the meniscus prosthetic device comprises a bioactive coating, and further comprising:

promoting tissue growth using the bioactive coating.

4. The method of claim 1, further comprising:

limiting deformation of the meniscus prosthetic device using the filament.

5. The method of claim 1, wherein the central body portion comprises a recess, and further comprising:

lubricating the upper articulating bearing surface based on accumulation of synovial fluid within the recess.

6. The method of claim 1, wherein the perimeter of the meniscus prosthetic device comprises a first portion and a second portion.

7. The method of claim 6, wherein the first and the second portions of the perimeter together completely surround the central body portion.

8. The method of claim 6, wherein the first portion and the second portion each have an increased thickness relative to the central body portion.

9. The method of claim 8, wherein the first portion has a first thickness and the second portion has a second thickness different than the first thickness.

10. The method of claim 6, wherein the second portion extends between first and second ends of the first portion.

11. The method of claim 6, wherein at least one of the first portion or the second portion of the perimeter at least partially surrounds central body portion in a semi-ellipsoidal manner.

12. The method of claim 1, wherein the filament is positioned within a recess in the perimeter.

* * * * *